United States Patent [19]

Jupe et al.

[11]  4,362,604

[45]  Dec. 7, 1982

[54] PROCESS FOR THE PREPARATION OF PYROCATECHOL AND HYDROQUINONE

[75] Inventors: Christoph Jupe, Cologne; Helmut Waldmann, Leverkusen; Jürgen Baumert, Cologne; Günther Schümmer, Stommeln, all of Fed. Rep. of Germany

[73] Assignee: Bayer Aktiengesellschaft, Leverkusen, Fed. Rep. of Germany

[21] Appl. No.: 292,854

[22] Filed: Aug. 14, 1981

[30] Foreign Application Priority Data

Aug. 22, 1980 [DE] Fed. Rep. of Germany ....... 3031736

[51] Int. Cl.$^3$ .............................................. B01D 3/14
[52] U.S. Cl. ....................................... 203/75; 203/77; 203/78; 203/80; 203/82; 203/84; 203/93; 203/94; 568/752; 568/753
[58] Field of Search ....................... 568/751, 752, 753; 203/71, 73, 80, 91, 74, 75, 77, 78, 82, 84, 94, 98

[56] References Cited

U.S. PATENT DOCUMENTS 4,308,112 12/1981 Jupe et al. ............................. 203/80

Primary Examiner—Frank Sever
Attorney, Agent, or Firm—Sprung, Horn, Kramer & Woods

[57] ABSTRACT

A process for the isolation of hydroquinone, pyrocatechol, phenol and carboxylic acid from the reaction mixture containing the same such as one obtained by reaction of phenol with percarboxylic acid is disclosed. The reaction mixture is fed to a first rectification column and subjected to distillation whereby there is obtained a bottoms product containing pyrocatechol, hydroquinone and phenol. The top product is largely condensed and recycled, there being withdrawn from the top of the rectification column a mixture comprising phenol and carboxylic acid. The phenol and carboxylic acid mixture are continuously fed to a second rectification column where carboxylic acid is separated from phenol and substantially pure phenol is withdrawn from the stripping section and/or bottom of the second rectification column.

13 Claims, No Drawings

PROCESS FOR THE PREPARATION OF PYROCATECHOL AND HYDROQUINONE

The present invention relates to a process for the preparation of pyrocatechol and hydroquinone.

Pyrocatechol and hydroquinone are industrially important organic fine chemicals which are used directly, for example in photographic developers, and also as intermediate products, for example, for dyestuffs, polymerisation inhibitors, pharmaceuticals and plant protection agents (see Kirk-Othmer, Encyclopedia of Chemical Technology, 2nd edition, Volume 11, pages 462 to 492, particularly pages 469 and 488 (1966)).

The search for economical and simple preparation processes has led, inter alia, to a series of phenol oxidation processes, which yield pyrocatechol and hydroquinone as coupled products (see, for example, German Offenlegungsschrift Nos. 2,658,943, 2,410,742, 2,364,181, 2,658,545, 2,332,747, 1,593,968, 2,633,302, 2,064,497, 2,150,657, 2,167,040, 2,341,743, 2,407,398, 1,543,953 and 2,404,114, and Japanese patent application No. 54 55,530 and 54 66,629, and T. Tsuchiya, M. Andoh and J. Imamura, Nipp. Kag. Kaishi 1979, 3, pages 370 to 374).

In these processes, phenol is reacted with a peroxidic reagent, for example with hydrogen peroxide or a percarboxylic acid, which are, in most cases, dissolved in a solvent which is lower-boiling than phenol. A further characteristic of these processes consists in the fact that, to avoid over-oxidation, a deficiency of oxidizing agent, relative to the compound to be hydroxylated, is employed. This has the consequence that unreacted phenol is contained in the reaction mixture after the reaction.

Particularly favourable conditions result if the hydroxylation is carried out with percarboxylic acids, since in this process, for example, the reactions can be carried out without addition of catalysts (see for example German Offenlegungsschrift No. 2,658,943).

In the previously mentioned literature, reference is mainly made to the usual methods, especially to distillation, extraction and crystallization, for working up the reaction mixtures which are present after the hydroxylation. More exact data are largely lacking.

Detailed data for the reaction and working-up are to be found in two publications which describe industrial plants for the preparation of pyrocatechol and hydroquinone from phenol and hydrogen peroxide, namely in Jean Varagnat, Ind. Eng. Chem., Prod. Res. Dev., Volume 15, No. 3, pages 212 to 215 (1976) and P. Maggioni and F. Minisci, La Chimica et l'Industria, Volume 59, No. 4, pages 239 to 242 (1977).

In the publication by J. Varagnat, the separation of the reaction mixture by distillation in a sequence of five rectification columns is described. Phenol and further auxiliary and accompanying substances are obtained in four columns as top products and are re-used, whilst pyrocatechol and hydroquinone are separated in a fifth column, and the hydroquinone is then subjected to a crystallization.

The reaction mixture is also worked up mainly by distillation according to the process described by P. Maggioni and F. Minisci. After a stepwise evaporation in three separate evaporators connected in sequence, with progressively lower pressure down to 13 mbars, the remaining working-up of the mixture is effected in two rectification columns. In the first column, phenol is obtained for recycling, and in the second column, the products pyrocatechol and hydroquinone are obtained.

If the effort invested in the industrial working-up of reaction mixtures of phenol and peroxidic reagents for obtaining pyrocatechol and hydroquinone is considered, it will be found that, in the two previously described processes, separation of the unreacted phenol, especially, requires a great effort.

A process for the preparation of pyrocatechol and hydroquinone by reaction of phenol with percarboxylic acids with 1 to 4 carbon atoms, with a molar ratio of phenol to percarboxylic acid, before the reaction, of from 5:1 to 50:1, and working-up of the mixture, which is present after the reaction and, if desired, after further treatment, and which contains unreacted phenol, the carboxylic acid corresponding to the percarboxylic acid, pyrocatechol, hydroquinone and which may contain further constituents, using continuously operated rectification apparatuses, has now been found, which is characterized in that (a) the mixture is continuously fed to a first rectification column at a point between the stripping section and the rectifying section, the rectification column having up to 20 separation stages in the stripping section and 5 to 30 separation stages in the rectifying section, this column is operated under a pressure between 0.01 and 2 bars, between 20 and 95% by weight of the top product or the same quantity by weight of phenol, or of a product stream, containing phenol, from the process, or the same quantity by weight of a mixture of top product and phenol and/or a product stream, containing phenol, from the process, condensed as a liquid reflux, is recycled to the top of the column, a top product, which contains phenol and carboxylic acid and which may contain further constituents, which are lower-boiling than phenol, is withdrawn, and a bottom product is taken off, which contains pyrocatechol, hydroquinone, phenol and which may contain further constituents, and pyrocatechol and hydroquinone are recovered from the bottom product, and (b) the top product of the first rectification column is continuously fed to a second rectification column at a point between the stripping section and the rectifying section, the second rectification column having 5 to 35 separation stages in the rectifying section and 8 to 35 separation stages in the stripping section, this column is operated under a pressure between 0.02 and 2 bars, 20 to 95% by weight of the product collecting at the head, condensed as a liquid reflux, is recycled to the top of the column, a top product, which is practically free of phenol and which contains the carboxylic acid corresponding to the percarboxylic acid, is withdrawn, and a substantially pure phenol is taken off from the stripping section and/or the trough of the column.

A mixture which can be employed in the working-up by distillation, according to the invention, can be obtained, according to known processes, by reacting phenol with a percarboxylic acid with 1 to 4 carbon atoms, with a molar ratio of phenol to percarboxylic acid, before the reaction, of from 5:1 to 50:1, and by further treating the reaction mixture thereby obtained, if desired.

Monopercarboxylic acids, which are derived from monocarboxylic acids with the same number of carbon atoms, can be employed as the percarboxylic acid, for example peracetic acid or perpropionic acid. It is possible to employ only one percarboxylic acid by itself. However, a mixture of several percarboxylic acids with 1 to 4 carbon atoms can also be employed. A percarboxylic acid with 2, 3 or 4 carbon atoms is preferably employed, in each case by itself. Peracetic acid or perpropionic acid is particularly preferably employed, in each case by itself.

The reaction of phenol with percarboxylic acid is carried out, in general, to an extensive conversion of the percarboxylic acid. A conversion of percarboxylic acid of over 99% is preferred, and a conversion of more than 99.7% is particularly preferred, so that the mixture to be employed in the working-up by distillation, according to the invention, is largely free of percarboxylic acid.

If necessary, the mixture obtained from the reaction of phenol and percarboxylic acid can be subjected to a further treatment before being used in the working-up by distillation, according to the invention. For example, this can consist in neutralizing phosphoric acid in a reaction mixture of phenol and per-acid, before the distillation (see German Offenlegungsschrift No. 2,364,181). Another type of further treatment can consist, for example, in withdrawing from the liquid reaction mixture a gas phase which can contain, for example, oxygen and carbon dioxide as by-products of the hydroxylation reaction.

The mixtures to be employed in the working-up by distillation, according to the invention, contain phenol, the carboxylic acid corresponding to the percarboxylic acid, pyrocatechol, hydroquinone and may contain further constituents.

The content of phenol can vary within wide limits. In general, it is between 5 and 95, preferably between 20 and 90% by weight. However, it is also possible to employ mixtures with phenol contents differing from the above in the working-up by distillation, according to the invention.

For the economical operation of the working-up by distillation, according to the invention, the ratio by weight of phenol to pyrocatechol and hydroquinone in the mixture to be employed is of importance. In general, it is advantageous to employ, in the working-up by distillation, according to the invention, mixtures in which this ratio by weight is as small as possible. Because of the fact that the hydroxylation of phenol is advantageously carried out in the presence of a large excess of phenol, considerable quantities of unreacted phenol are however present, in general, in the reaction mixtures after the hydroxylation. Such reaction mixtures, in which the ratio by weight of phenol to pyrocatechol and hydroquinone is, for example, in the range of 3.4 to 100:1 or 6 to 40:1, are suitable for use in the working-up by distillation, according to the invention. The further treatment of the reaction mixture from the hydroxylation, which treatment is carried out if desired, for example, the neutralization of phosphoric acid which is present, or separating off a gas phase, is carried out, in general, in such a manner that the proportions of phenol to pyrocatechol and hydroquinone remain in the previously mentioned limits.

It is preferable not to change the ratio, present after the reaction, of phenol to pyrocatechol and hydroquinone, by means of a further treatment, which is carried out if desired. Thus, the unreacted phenol is preferably largely removed after the reaction by means of the working-up by distillation, according to the invention.

Reaction mixtures in which the molar ratio of phenol to percarboxylic acid was between 8 and 25:1 in use in the reaction are particularly suitable for use in the working-up by distillation, according to the invention.

The content of carboxylic acid in the mixture to be employed can likewise vary within wide limits. It can be, for example, between 1 and 95% by weight, or between 5 and 40% by weight.

The content of pyrocatechol and hydroquinone in the mixture to be employed can vary between very small values and about 21% by weight. Although as large a content as possible of pyrocatechol and hydroquinone is in itself preferred, because of the large proportions, as a rule, of unreacted phenol, and not inconsiderable proportions of carboxylic acid, and owing to other constituents which may be present, in many cases only mixtures which have a content of pyrocatechol and hydroquinone of below 20% by weight can be employed in the process according to the invention. The content of dihydroxybenzenes in the mixture to be employed is frequently between 0.5 and 10% by weight.

The ratio by weight of pyrocatechol and hydroquinone in the mixture to be employed in the working-up by distillation, according to the invention, is not of particular importance. In general, this ratio is between 0.1 and 10 or between 0.8 and 4.

The mixtures to be employed in the working-up by distillation, according to the invention, can optionally contain further constituents, in addition to the constituents hitherto listed. The content of further constituents can vary within wide limits. It can be, for example, between 0.1 and 50% by weight. The possibly present further constituents can have boiling points below or above the boiling point of phenol. They can also be very high-boiling or non-distillable. If further constituents wholly or partly form phenol-containing azeotropic mixtures which may also contain other, already-mentioned constituents of the mixture to be employed, under the conditions of the working up by distillation, according to the invention, their proportion in the mixture to be employed is to be kept so small that not all the phenol can be azeotropically distilled from the mixture to be employed.

Mixtures are preferred, in the working-up of which by distillation no phenol-containing azeotropic mixtures occur as top products. Furthermore, mixtures are preferably employed in the working-up by distillation, according to the invention, which, if they contain further constituents, only contain those further constituents which have boiling points either lower than the boiling point of phenol or higher than the boiling point of pyrocatechol. This means that those mixtures are preferred in which no compounds which boil between phenol and pyrocatechol are contained.

Mixtures which, if they contain any further constituents at all, only contain those further constituents which boil either lower than the lowest-boiling carboxylic acid contained in the mixture or higher than pyrocatechol, are particularly preferred. Mixtures are very particularly preferred, which contain those further constituents which boil lower than the lowest-boiling carboxylic acid present in the mixture, and which, if they contain yet other further constituents, only contain those other further constituents which boil either above hydroquinone or are non-distillable under the conditions of the working-up by distillation, according to the invention.

The optionally present further constituents can have entered the mixture to be employed in various ways. They can be chemically of very variable nature and can be, in part, of a nature which cannot even exactly be determined chemically. The following may be mentioned as examples of further constituents:

Solvents, for example from a percarboxylic acid solution employed for the hydroxylation reaction, for example water, benzene, chlorobenzene, 1,2-dichloropropane, 1,2-dichloroethane, ethyl acetate, acetic acid and/or propionic acid;

oxygen, which can originate, for example, from the decomposition of a peroxidic reagent;

carbon oxides (carbon monoxide and/or carbon dioxide), which can have been formed, for example, by overoxidation in the hydroxylation reaction;

salts of acids, which can have been formed, for example, in the neutralization of acids in the reaction mixture;

trihydroxybenzenes, which can have been formed, for example, in the hydroxylation reaction as by-products;

substances which are higher-boiling than hydroquinone or which are non-distillable, which, for example, behave similarly to lignite or to humic acids or have a tar-like behaviour, and which can have been formed, for example, as by-products of the hydroxylation reaction;

phosphorus-containing substances which are higher-boiling than hydroquinone or which are non-distillable, or other substances which are higher-boiling than hydroquinone and which have metal-complexing properties, which, for example, can have been added to the hydroxylation mixture or which can have been formed from added complex-forming substances.

The optionally present further constituents are preferably of such a nature that, under the conditions of the working-up by distillation, according to the invention, they cannot react, or only a small part of them can react, with themselves, with one another or with other constituents of the mixture to be employed.

In general, at most 10% by weight, particularly preferably less than 5% by weight, of any component of the mixture to be employed is consumed by reaction during the working-up by distillation, according to the invention.

For the operation of the working-up by distillation, according to the invention, the previously described mixture is continuously fed, between the rectifying section and the stripping section, to a first rectification column.

This first rectification column has up to 20 separation stages in the stripping section and 5 to 30 separation stages in the rectifying section. 5 to 20 separation stages are preferred for the rectifying section, and 7 to 16 separation stages are particularly preferred for this section. A small number of separation stages is preferred for the stripping section.

It has proved advantageous to feed mixtures which contain high-boiling or non-distillable organic substances, which, for example, behave similarly to lignites or to humic acids, or have a tar-like behaviour, to the sump region of the first rectification column. Such a position of the feed point results in a stripping section with the effect of up to one separation stage.

In the above and in the text which follows, a separation stage is defined as a column section, the separating action of which, in a rectification, is capable of establishing the equilibrium between ascending vapour phase and descending liquid phase, as is explained, for example, in "Organikum, Organisch-Chemisches Grundpraktikum" ("Organic Chemistry, Fundamental Practical Principles"), 15th edition (reprint), VEB Deutscher Verlag der Wissenschaften, Berlin, 1977, pages 63 to 69, particularly pages 66 and 67.

The state established at the phase boundary in the sump is, for various reasons, in practice more or less removed from an ideal equilibrium state, so that at this point the separation action is below that of the ideal value of one separation stage.

Although small amounts of low-boiling constituents from the feed mixture can still be present in the bottom product of such a rectification, the aim of the working-up by distillation, according to the invention can be achieved, namely, a separation of the mixture employed, with recovery of phenol and, if present, of further substances, with reduced effort.

For mixtures which contain neither high-boiling nor non-distillable substances, it is advantageous if the first rectification column contains a stripping section with 6 to 12 separation stages.

At the bottom of the first rectification column, a mixture is taken off, which contains phenol, if appropriate traces of constituents which are lower-boiling than phenol, pyrocatechol, hydroquinone, and, if appropriate, further constituents, the boiling points of which are higher than the boiling point of the phenol, and from this mixture pyrocatechol and hydroquinone are recovered.

The bottom product preferably does not contain more than 5% by weight of constituents, the boiling points of which are lower than the boiling point of the phenol, and a content of less than 2.5% by weight of such easily-boiling solvents is particularly preferred. The content of phenol in the bottom product can vary within wide limits, for example between 10 and 90% by weight. A content of between 30 and 70% by weight is preferred, and a content of between 40 and 65% by weight is very particularly preferred.

In the operation according to the invention of the first rectification column, easily-boiling solvents and a large part of the phenol employed can be distilled off under mild conditions. The sump temperature can be kept lower in this process than in the case in which all the phenol already had to be removed in this stage, via the head. Thereby, the thermal load for the bottom product is kept small. This load is principally caused by the temperature at which the quantity of energy necessary for evaporation is conducted into the evaporator and for which the bottom product largely serves as a heat transferring agent. A further advantage of the procedure, according to the invention, for the first rectification column is the lowering of the solidification point of the bottom product, so that the effort involved in manipulating the bottom product as a liquid is small. It is, in fact, preferred to feed the bottom product of the first rectification column as a liquid to the subsequent recovery of pyrocatechol and hydroquinone.

The recovery of pyrocatechol and hydroquinone from the bottom product of the first rectification column can be effected in a manner which is in itself known, for example, by distillation, rectification, crystallization or extraction, or any desired combination of several of these methods, whereby, if desired, residual phenol and constituents which are lower-boiling than phenol can also be isolated. It is preferable, in further rectification columns, to obtain and to take off first the low-boiling solvent residues and phenol, then pyrocatechol and then hydroquinone, as "on-specification" distillates. A process corresponding to this route is described, for example, in the U.S. application Ser. No. 166,270, filed July 2, 1980, entitled "Process for the Isolation of Pyrocatechol and Hydroquinone" assigned to the assignee hereof, the disclosure of which is hereby incorporated herein by reference. According to that process the pyrocatechol and hydroquinone are separated from one another by rectification of pyrocatechol as overhead followed by evaporation of the hydroquinone from the rectification bottoms. It has been found that there are no difficulties in working up, according to the process described, even those mixtures which contain, in addition to the constituents mentioned in the patent application, a certain proportion of constituents which are lower-boiling than phenol.

The first rectification column is operated under a pressure of between 0.01 and 2 bars, but taking into consideration the temperature limits described in the following text. This column is preferably operated between 0.1 and 1.2 bars, very particularly preferably between 0.5 and 1.1 bars.

The temperatures in the column are established according to the pressure and the composition of the substance mixtures at the various points of the column. The whole working-up by distillation, according to the invention, is advantageously operated in such a manner that a temperature of 250° C. is not exceeded at the product end. Temperatures between 230° C. and 250° C. at the product end are preferably to be reached at most for a short time. It is very particularly preferred always to maintain temperatures at the product end of below 230° C. The lower limit for temperature or pressure is set by the solidification point of the top product. The temperature at the head of the column, determined by pressure and composition of the top product, must be above the melting point of the top product, otherwise a rectification yielding a liquid reflux consisting of condensed top product cannot be carried out.

If desired, a part of the vapor produced at the head of the column, is condensed and returned to the column as a liquid reflux. The part of the top product which is not returned to the column as a reflux is taken off.

The proportion of reflux to take-off is between 0.25 and 19. A reflux ratio of between 0.3 and 10 is preferred, and a reflux ratio of between 0.4 and 2.5 is very particularly preferred.

Instead of condensed to product, the same quantity of liquid phenol or of a liquid product stream, containing phenol, from the process can also be fed as a reflux to the head of the first rectification column. It is possible, for example, to take off an appropriate product stream from the stripping section of the second rectification column of the working-up by distillation, according to the invention. Such a product stream can preferably be taken off from the bottom of the second rectification column. Mixtures of top product and liquid phenol and/or a product stream, containing liquid phenol, from the process can also be fed in the given quantity to the head of the first rectification column.

It is preferable to select the head temperature of the first rectification column so that it is at least 10° to 15° C. above the bottom temperature of the second rectification column of the working-up by distillation, according to the invention, and to feed the vapours of the top product of the first column wholly or partly as a heat medium to a heat exchanger, which functions as a evaporator for the second rectification column, and wholly or partly to condense the vapours in this evaporator, and, if desired, further to cool the condensate. This coupling of both columns makes it possible to manage with a minimum of externally derived energy for heating the evaporators.

In order to better utilise the energy content of the vapours at the head of the first rectification column, the so-called "vapour compression" process can also be employed, and a further evaporator can be heated with the vapours which have been brought to a higher pressure level and temperature level. A suitable further evaporator is preferably the evaporator of the second rectification column of the working-up by distillation, according to the invention. However, it is also possible to heat in this manner another evaporator with a suitable temperature level. If appropriate, it can further be advantageous to feed to the first rectification column, at a suitable point, further product streams from the working-up by distillation, according to the invention, or from working-up stages subsequent to this, as liquid or vapour or as a liquid/vapour mixture. Particularly suitable for this purpose are product streams which are present in a small quantity compared with the starting mixture in the first rectification column, and which contain phenol.

One or several of the following product streams are very particularly preferably wholly or partly returned to the first rectification column:

the distillate which contains residual low-boiling solvents and phenol and which is obtained if the bottom product of the first rectification column is freed, in a further rectification column, of residual phenol and remaining low-boiling solvents;

the bottom product of the second rectification column of the working-up by distillation, according to the invention, which bottom product contains predominantly phenol, in the case in which the bulk of phenol is taken off above the sump of the second rectification column;

the product which is obtained if the constituents which are lower-boiling than phenol have been separated off, for example by rectification, from the top product of the second rectification column; the last-mentioned product can also be fed, for example, to the second rectification column of the working-up by distillation, according to the invention, as an additional feed.

Suitable for the input of further product streams into the first rectification column are those points at which the product streams inside the column are as similar as possible in their composition to the product streams additionally to be fed in.

The top product of the first rectification column contains phenol, carboxylic acid and may contain further constituents, the boiling points of which are lower than the boiling point of phenol.

A quantity of phenol is preferably taken off with the top product so that a phenol content between 30 and 70% by weight is present in the bottom product of the first rectification column. A quantity of phenol is very particularly preferably taken off with the top product of the first rectification column so that a phenol content of between 40 and 65% by weight is present in the bottom product.

The product taken off at the head of the first rectification column is continuously fed, if desired after the described utilisation of its heat content, to a second rectification column, between rectifying section and stripping section.

This second rectification column has 5 to 35 separation stages in the rectifying section and 8 to 35 separation stages in the stripping section. A rectification column with 10 to 30 separation stages in the stripping section and 10 to 20 separation stages in the rectifying section is preferred. This column is operated at a pressure of between 0.02 and 2 bars, preferably between 0.05 and 1.2 bars, and particularly preferably between 0.15 and 1.1 bars.

The top product of the second rectification column is partly condensed, and is returned in liquid form as a reflux to the top of this rectification column. The part which is returned as a reflux to the column is between 20 and 95% by weight of the total top product. 50 to 90% of the top product is preferably used as a reflux, and 60 to 85% by weight of the top product is particularly preferably used as a reflux.

The top product is largely free of phenol and contains the carboxylic acid. A residual phenol content in the top product of less than 1 part by weight of phenol to 1,000 parts by weight of carboxylic acid is preferred, and a residual phenol content of between 10 and 500 parts by weight of phenol to 1 million parts by weight of carboxylic acid is very particularly preferred. If appropriate, the top product of the second rectification column can contain further constituents which are lower-boiling than phenol.

The portion of the top product which is not used as a reflux is taken off and can be used as desired. In general, it is condensed and is further used in liquid form.

The carboxylic acid from the top product of the second rectification column is preferably recovered and again used for the preparation of percarboxylic acid, which can be used, if desired, for the hydroxylation of phenol. Likewise, it is preferable to recover any content of solvent from the top product of the second rectification column and to use it again, for example for the preparation of percarboxylic acid solutions, which can be used, if desired, for the hydroxylation of phenol. The recovery of carboxylic acid and, if present, of the solvent or solvents can occur in any desired manner. Carboxylic acid and, if appropriate, solvents are preferably recovered, by further rectification, in a form which is sufficiently pure for a repeated utilisation.

Virtually pure phenol is taken off from the stripping section of the second rectification column. The phenol can be exclusively taken off as a bottom product, but a part of the phenol can also be taken off, between feed and bottom as a liquid or vapour or as a liquid/vapour mixture. The largest part of the phenol to be taken off from the stripping section is preferably taken off as a liquid side stream from the stripping section, above the sump of the column. The phenol taken off from the stripping section of the second rectification column is very particularly preferably divided in such a manner that between 65 and 99.9% by weight are taken off as a side stream, and an amount corresponding to the remainder is taken off as a bottom product. In general, every point in the stripping section between 15 and 80% of the total effective length of the stripping section (counted from the sump upwards) is suitable for the take-off of a side stream of phenol.

A side stream of phenol is preferably taken off between 20 and 60% of the effective length of the stripping section, counted from the sump upwards. The phenol which has been taken off from the stripping section of the second rectification column can contain carboxylic acid. In general, the content of carboxylic acid in the phenol taken off is under 5% by weight, preferably under 1% by weight, very particularly preferably between 10 and 1500 ppm by weight.

The phenol taken off can be put to any desired use. The phenol is preferably condensed and, in liquid form, if desired after further treatment, wholly or partly reused in the reaction with percarboxylic acid, and a phenol portion, which, if desired, is not fed back into the reaction with percarboxylic acid, is fed to the first rectification column of the working-up by distillation, according to the invention. Phenol taken off as a side stream, if desired after further treatment, is very particularly preferably again employed, in liquid form, in the reaction with percarboxylic acid.

Furthermore, it can be advantageous to feed, as an additional feed, a phenol-containing residue, as can be produced, for example, in the further working-up of the product taken off at the head of the second rectification column, to the second rectification column at a suitable point. However, it is also possible to feed such a product stream to the first rectification column, as an additional feed.

With respect to the temperature limitations, the data stated for the first rectification column applies for the second rectification column.

All customary rectification columns, for example packed columns, sieve tray columns or bubble-cap tray columns, are suitable for carrying out the working-up by distillation, according to the invention. Columns with fabric or other packings are also well suited. Columns can also be used which contain various installations or packing material in various sections. Likewise, the type of evaporator associated with the columns is not decisive for carrying out the working-up by distillation, according to the invention, since all current types of evaporator can be employed, for example tubular heat exchangers or falling film evaporators with forced circulation.

All industrially customary materials, which are sufficiently stable to the substances to be separated, in the temperature range up to about 250° C., can be employed for the manufacture of the rectification apparatuses. Glass, titanium and high-alloy refined steels with chromium and/or nickel contents of above 10% by weight in each case, for example materials according to DIN (German Industrial Standards) 1.4571 or DIN (German Industrial Standards) 1.4439, are examples of suitable materials.

An advantageous form of operation of the working-up by distillation according to the invention is represented in the following:

The mixture to be employed is obtained by reaction of phenol with a solution of peracetic acid or perpropionic acid in a solvent which is lower-boiling than acetic acid, such as benzene, ethyl acetate or 1,2-dichloropropane, with an initial molar ratio of 8 to 25 mols of phenol per mol of percarboxylic acid. The mixture to be employed thus contains:
8 to 15 parts by weight of solvent which is lower-boiling than acetic acid
0.5 to 2 parts by weight of water
3 to 8 parts by weight of acetic acid or propionic acid
50 to 90 parts by weight of phenol
1.5 to 4 parts by weight of pyrocatechol
0.6 to 3 parts by weight of hydroquinone
0.2 to 2 parts by weight of constituents which are higher-boiling than hydroquinone or non-distillable, which contain 2 to 4% by weight of inorganic salts, and which are mainly composed of carbon, oxygen and hydrogen, containing these elements in about the following ratio: 60 to 80 parts by weight of carbon, 15 to 25 parts by weight of oxygen and 2 to 8 parts by weight of hydrogen.

This mixture is fed, between stripping section and rectifying section, to a packed rectification column or sieve tray rectification column of glass or stainless steel, with 15 to 20 separation stages in the rectifying section and up to 20 separation stages in the stripping section.

The column is operated at a pressure of between 0.4 and 1.2 bar, and the ratio of reflux to take-off is between 0.2:1 and 2:1. The product taken off at the bottom of the column contains 40 to 65% by weight of phenol and virtually all constituents, which are higher-boiling than phenol, of the mixture employed in the column, and not more than 3% by weight of portions which are lower-boiling than phenol. Pyrocatechol and hydroquinone are isolated from the bottom product by further rectifications, for example according to the process described in the German patent application P 29 28 553.8. The top product of the first rectification column contains the bulk of the phenol employed in the column, and by far the predominant part of the solvent and the acetic acid or propionic acid.

The top product of the first rectification column is fed to a second rectification column of glass or stainless steel. This column has 15 to 25 separation stages in the rectifying section and 15 to 25 separation stages in the stripping section. A take-off point for a liquid side stream is situated in the region of the 5th to 7th separation stage of the stripping section, counted from the bottom up. The column is operated under a pressure of from 0.1 to 1 bar, and the ratio of reflux to take-off is between 0.8:1 and 5:1.

Solvent, water and acetic acid and/or propionic acid are withdrawn in a mixture as the top product. The phenol content in this mixture is below 1% by weight. Liquid phenol is taken off from the stripping section. The total take-off results from a side stream take-off of phenol with up to 3% by weight of acetic acid or propionic acid, and a bottom take-off of phenol with less than 0.1% by weight of acetic acid or propionic acid. The proportion of side stream take-off to bottom take-off is between 80:20 and 99.9:0.1.

The product taken off at the bottom is either fed to the reaction of phenol with the solution of peracetic acid or perpropionic acid, or serves as an additional reflux for the first rectification column. The phenol taken off as a side stream is exclusively fed to the reaction of phenol with the percarboxylic acid. If desired, the phenol to be fed back into the reaction is wholly or partly subjected, before the reaction, to a further treatment, for example with ion exchangers, as described in the U.S. Ser. No. 164,444, filed June 30, 1980, entitled "Process for the Preparation of Polyhydric Phenols", assigned to the assignee hereof, the disclosure of which is hereby incorporated herein by reference. According to that process a polyhydric phenol is obtained by hydroxylation of a phenol with a peroxidic hydroxylating agent in a process wherein before the hydroxylation, all or some of the mixture to be hydroxylated is treated with a cation exchanger such as one which contains $SO_3^-$ and/or $COO^-$ groups.

The mixture which is taken off as a top product of the second rectification column, and which contains the solvent, water, acetic acid or propionic acid, and not more than 1% by weight of phenol, is further rectified to recover solvent and acetic acid or propionic acid as pure substances, and to use them again for the preparation of a solution of peracetic acid or perpropionic acid. The bottom product of this subsequent rectification, which product is present after separation of solvent and acetic acid or propionic acid, and which contains traces of phenol, is fed, as an additional feed, to the first or second columns of the working-up by distillation, according to the invention.

Compared to known processes for the working-up of similar mixtures, the effort for separating off and recovering phenol and constituents which are lower-boiling than phenol is reduced in the process according to the invention. The working-up by distillation, according to the invention, has, in addition, the advantage that the high-boiling substances occuring in the process, which are, in general, high-boiling oxidation products of the phenol, remain dissolved and are deposited neither in the evaporators, nor in the sumps, nor elsewhere in the column, so that blockages are avoided and deposits remain limited to a very small extent.

This is particularly the case if mixtures containing high-boiling constituents and/or non-distillable substances are fed into the sump region of the first rectification column.

It is surprising that, with a process which is simpler than known processes, a phenol can be obtained, which can be employed again, without further complicated measures, in the reaction with percarboxylic acid. The specialist would have rather expected, with a knowledge of the known processes, that an improved operation of the process would only be possible with an increased effort.

EXAMPLE

The example which follows is intended to illustrate the invention in more detail, without in any way limiting it.

12.295 kg/h of a mixture, which was obtained after reaction of phenol with a solution of perpropionic acid in a mixture of benzene and propionic acid, and after separating out a gas phase after the reaction, was continuously fed to a rectification column, between the sump and the body of the column.

The following components were determined in the mixture fed to the column:

| benzene | 10.67% by weight |
|---|---|
| propionic acid | 5.28% by weight |
| water | 0.12% by weight |
| phenol | 80.02% by weight |
| pyrocatechol | 2.14% by weight |
| hydroquinone | 1.38% by weight |

The undetermined remainder of 0.39% by weight consists of various substances. In addition to traces of constituents which are lower-boiling than phenol, this remainder contains only substances which are higher-boiling than hydroquinone, and non-distillable substances.

The rectification column was made of V4A stainless steel (material corresponding to DIN (German Industrial Standard) 1.4571), and had an effective length of 5,200 mm.

It contained within, from the bottom upwards:

8 × 8 mm glass Raschig rings
for a length of 2,000 mm

```
4 sieve trays
   for a length of 1,200 mm
8 × 8 mm glass Raschig rings
   for a length of 2,000 mm.
```

The internal column diameter was 100 mm.

Before entry into the column, the mixture was heated to a product temperature of 142° C. in a tubular heat exchanger of V4A stainless steel, and the heat exchanger was heated with steam at 6 bars.

The column was maintained under a pressure of 760 mbars, measured at the head of the column. An evaporator, which was likewise made of V4A stainless steel, and was constructed as an annular gap evaporator, was situated at the bottom of the column.

The vaporiser was heated with thermal oil at 230° C., and the throughput of thermal oil was regulated in such a manner that a constant temperature profile was maintained in the column. Temperatures of between 185° and 189° C. were measured in the sump, and the temperature at the head of the column was 163° C.

A quantity of 1.041 kg of product per hour was produced at the bottom, and a quantity of 18.173 kg of product per hour was produced at the head.

The bottom product was taken off, and worked up, in further rectifications according to the process described in the German patent application P 29 28 553.8, to obtain pyrocatechol and hydroquinone. A product stream of 0.563 kg/h, which is produced in this working-up and which predominantly consists of phenol, was fed, as an additional liquid reflux, to the first rectification column, 1,000 mm below the head of the column; the following constituents were analysed in this product stream:

| benzene | 0.04% by weight |
|---|---|
| pyrocatechol | 0.08% by weight |
| propionic acid | 2.03% by weight |
| water | 1.20% by weight |
| phenyl propionate | 0.05% by weight |
| phenol | 96.60% by weight |

Furthermore, a further product stream of 0.066 kg/h, which was taken off as the bottom product of the 2nd rectification column, was also fed to the 1st rectification column at the height of the feed of the principal amount, between the sump and the actual column. The following constituents were analysed in this product stream:

| phenol | 99.54% by weight |
|---|---|
| propionic acid | 0.04% by weight |
| water | 0.01% by weight |
| phenyl propionate | 0.41% by weight |

At the head of the 1st rectification column, a quantity of 18.173 kg/h of product was produced, in which the following constituents were analytically determined:

| phenol | 83.38% by weight |
|---|---|
| propionic acid | 5.37% by weight |
| benzene | 11.04% by weight |
| water | 0.22% by weight |

6.295 kg/h of this product, condensed as a liquid reflux, was returned to the head of the column. The quantity of 11.878 kg/h, which was taken off, was continuously fed to a second rectification column, between the stripping section and the rectifying section.

This 2nd rectification column was made of V4A stainless steel, and had an internal diameter of 100 mm. In the rectifying section, the column was filled for a length of 2,000 mm with 8×8 mm glass Raschig rings. The stripping section contained, considered from the feed, 8×8 mm glass Raschig rings for a length of 2,500 mm, and then, in a column section of 500 mm length, only an arrangement for taking off a liquid side stream (so-called "take-off cup"), and, following this, 8×8 mm glass Raschig rings for a length of 500 mm.

The evaporator of the column, the former likewise being made of stainless steel, had a coiled heat exchanger with a natural circulation, and was heated with steam at 10 bars. The regulation was effected by changing the steam pressure to maintain a constant temperature profile in the column.

A quantity of 8.821 kg/h was produced at the head, and the following components were analysed in this product:

| benzene | 66.87% by weight |
|---|---|
| propionic acid | 32.04% by weight |
| phenol | 0.01% by weight |
| water | 1.09% by weight |

After condensation, 6.861 kg/h were returned, as a liquid reflux, to the head of the column. The remaining top product was taken off and was worked up, in two further columns, to obtain benzene and propionic acid. The benzene thus obtained and the propionic acid thus obtained were used for the preparation of solutions of perpropionic acid in a mixture of benzene and propionic acid.

The residue of 0.004 kg/h, which remains after separating out propionic acid and all components which are lower-boiling than propionic acid, was again employed in the 2nd rectification column.

A liquid side stream of 9.855 kg/h was taken off via the appropriate device, and the following constituents were analysed in this side stream:

| phenol | 99.82% by weight |
|---|---|
| propionic acid | 0.13% by weight |
| water | 0.05% by weight |

This side stream was again fed to the reaction with perpropionic acid solution.

The quantity of 0.066 kg/h was taken off from the bottom of the 2nd rectification column.

This bottom product was fed to the 1st rectification column at the same height as the mixture to be employed in the working-up by distillation according to the invention.

What is claimed is:

1. In a process for the recovery of pyrocatechol and hydroquinone from a reaction mixture obtained by reacting phenol with a percarboxylic acid having 1 to 4 carbon atoms at a molar ratio of phenol to percarboxylic acid, before the reaction, of 5 to 50:1 in which the reaction mixture comprising unreacted phenol, carboxylic acid corresponding to the percarboxylic acid, pyrocatechol and hydroquinone is worked up in a plurality of rectification apparatuses, the improvement wherein:
   (a) the reaction mixture is continuously fed to a first rectification column at a point between the stripping section and the rectifying section, the rectification column having up to 20 separation stages in the stripping section and 5 to 30 separation stages in the rectifying stage, the column being operated at a pressure between 0.01 and 2 bars, between 20 and 95% by weight of the top product or the same quantity by weight of phenol or a product stream containing phenol from the process or the same quantity by weight of a mixture of top product and phenol and/or product stream containing phenol, from the process, being condensed and returned to the first rectification column as liquid reflux, withdrawing a top product comprising phenol and carboxylic acid corresponding to the percarboxylic acid employed in the reaction, withdrawing a bottom product comprising pyrocatechol, hydroquinone and phenol, recovering pyrocatechol and hydroquinone from the bottom products; and (b) feeding the top product of the first rectification column continuously into a second rectification column at a point between the stripping section and the rectifying section, the second rectification column having 5 to 35 separation stages in the rectifying section and 8 to 35 separation stages in the stripping section, said second rectification column being operated under a pressure between 0.02 and 2 bars, 20 to 95% by weight of the product collecting at the head of said second rectification column being condensed as liquid reflux and recycled to the top of the column, withdrawing a top product, substantially free of phenol and comprising carboxylic acid corresponding to the percarboxylic acid and taking off substantially pure phenol from the stripping section and/or the bottom of the column, whereby high boiling oxidation products of the phenol remain disolved and blockages are avoided.

2. A process according to claim 1, wherein mixtures containing a high-boiling or non-distillable organic substance are fed to the sump region of the first rectification column.

3. A process according to claim 1, wherein the mixture which is fed to the first rectification column is one obtained by reaction of phenol with peracetic acid or perpropionic acid.

4. A process according to claim 1, wherein the reaction mixture fed to the first rectification column contains a solvent for the percarboxylic acid.

5. A process according to claim 4, wherein said solvent is water, benzene, chlorobenzene, 1,2-dichloropropane, 1,2-dichloroethane, ethyl acetate, acetic acid, propionic acid or a mixture thereof.

6. A process according to claim 1, wherein the reaction mixture fed to the first rectification column contains benzene.

7. A process according to claim 1, wherein the reaction mixture, which is fed to the first rectification column is one obtained by reaction of phenol and percarboxylic acid in a molar ratio of phenol to percarboxylic acid of between 8 and 25:1.

8. A process according to claim 1, wherein the distillation in the first rectification column is carried out such that a bottom product containing 30 and 70% by weight of phenol is taken off from the first rectification column.

9. A process according to claim 1, wherein a temperature of below 230° C. is always maintained at the product end.

10. A process according to claim 1, wherein a liquid product stream is withdrawn from the stripping section or the bottom of the second rectification column and is refluxed to the head of the first rectification column.

11. A process according to claim 1, wherein vapors from the first rectification column are employed to heat the components introduced into the second rectification column.

12. A process according to claim 1, wherein a side stream is taken off from the stripping section of the second rectification column and is fed back into the reaction of the phenol with a percarboxylic acid.

13. In a process for the recovery of pyrocatechol and hydroquinone from a reaction mixture obtained by reacting phenol with a percarboxylic acid having 1 to 4 carbon atoms at a molar ratio of phenol to percarboxylic acid, before the reaction, of 5 to 50:1 in which the reaction mixture comprising unreacted phenol, carboxylic acid corresponding to the percarboxylic acid, pyrocatechol and hydroquinone is subjected to a further treatment and then worked up in a plurality of rectification apparatuses, the improvement wherein:

(a) the reaction mixture is continuously fed to a first rectification column at a point between the stripping section and the rectifying section, the rectification column having up to 20 separation stages in the stripping section and 5 to 30 separation stages in the rectifying stage, the column being operated at a pressure between 0.01 and 2 bars, between 20 and 95% by weight of the top product or the same quantity by weight of phenol or a product stream containing phenol from the process or the same quantity by weight of a mixture of top product and phenol and/or product stream containing phenol, from the process, being condensed and returned to the first rectification column as liquid reflux, withdrawing a top product comprising phenol and carboxylic acid corresponding to the percarboxylic acid employed in the reaction, withdrawing a bottom product comprising pyrocatechol, hydroquinone and phenol, recovering pyrocatechol and hydroquinone from the bottom products; and (b) feeding the top product of the first rectification column continuously into a second rectification column at a point between the stripping section and the rectifying section, the second rectification column having 5 to 35 separation stages in the rectifying section and 8 to 35 separation stages in the stripping section, said second rectification column being operated under a pressure between 0.02 and 2 bars, 20 to 95% be weight of the product collecting at the head of said second rectification column being condensed as liquid reflux and recycled to the top of the column, withdrawing a top product, substantially free of phenol and comprising carboxylic acid corresponding to the percarboxylic acid and taking off substantially pure phenol from the stripping section and/or the bottom of the column.

* * * * *

UNITED STATES PATENT AND TRADEMARK OFFICE
CERTIFICATE OF CORRECTION

PATENT NO. : 4,362,604
DATED : December 7, 1982
INVENTOR(S) : Christoph Jupe et al.

It is certified that error appears in the above—identified patent and that said Letters Patent is hereby corrected as shown below:

Col. 7, line 46      Delete "to" and insert --top--

Col. 7, line 66      Delete "a" and insert --an--

Col. 16, line 63     After "column" insert omitted words --, whereby high boiling oxidation products of the phenol remain dissolved and blockages are avoided--

Signed and Sealed this

Sixteenth Day of October 1984

[SEAL]

Attest:

GERALD J. MOSSINGHOFF

Attesting Officer      Commissioner of Patents and Trademarks